(12) United States Patent
McClintock et al.

(10) Patent No.: US 10,337,989 B2
(45) Date of Patent: Jul. 2, 2019

(54) SYSTEM AND METHOD TO DETECT VEHICLE EMISSIONS NONCOMPLIANCE

(71) Applicant: Opus Inspection, Inc., East Granby, CT (US)

(72) Inventors: Peter M. McClintock, Marina Del Rey, CA (US); Thomas J. Fournier, Tucson, AZ (US); Niranjan Vescio, Tucson, AZ (US)

(73) Assignee: Opus Inspection, Inc., East Granby, CT (US)

( * ) Notice: Subject to any disclaimer, the term of this patent is extended or adjusted under 35 U.S.C. 154(b) by 220 days.

(21) Appl. No.: 15/342,764

(22) Filed: Nov. 3, 2016

(65) Prior Publication Data

US 2017/0131202 A1  May 11, 2017

Related U.S. Application Data

(60) Provisional application No. 62/251,906, filed on Nov. 6, 2015.

(51) Int. Cl.
*G01N 21/3504* (2014.01)
*G01M 15/10* (2006.01)
(Continued)

(52) U.S. Cl.
CPC ...... *G01N 21/3504* (2013.01); *G01M 15/108* (2013.01); *G01N 33/0073* (2013.01);
(Continued)

(58) Field of Classification Search
CPC ........ G01M 15/108; G01N 2021/1793; G01N 2021/3513; G01N 21/3504; G01N 33/0073; H04N 7/183
See application file for complete search history.

(56) References Cited

U.S. PATENT DOCUMENTS 5,210,702 A    5/1993  Bishop et al.
5,319,199 A *  6/1994  Stedman ................ G01N 21/33
                                                    250/338.5
(Continued)

FOREIGN PATENT DOCUMENTS

WO    0026641 A1    5/2000

OTHER PUBLICATIONS

Commonly assigned co-pending U.S. Appl. No. 15/360,458, filed Nov. 23, 2016, entitled System and Method to Detect Emissions OBD False Failures.

*Primary Examiner* — Peter D Le
(74) *Attorney, Agent, or Firm* — Gardner, Linn, Burkhart & Ondersma LLP

(57) ABSTRACT

A system and method to rapidly perform emissions measurements of in-use vehicles being driven by the general public under normal driving use for determining whether the vehicles are performing in accordance to the regulatory standards by which they were certified. The system and method require no recruitment testing of in-use vehicles with potentially detectable connections, but instead incorporate a vehicle emissions remote sensing device that does not require mechanical or electrical connection to the vehicle, with the measured values being recorded and the vehicles identified, including based on, for example, make and model, engine size, engine combustion management technology and/or pollution control technology. The system and method additionally operates to perform data analysis on the collected data to identify abnormal emissions-related conditions of a particular make and model for the purpose of in-use surveillance, thus allowing actual emissions results to be detected, determined and compared for compliance with regulatory standards.

20 Claims, 2 Drawing Sheets

(51) Int. Cl.
*G01N 33/00* (2006.01)
*G06K 9/00* (2006.01)
*G06K 9/32* (2006.01)
*H04N 7/18* (2006.01)
*G01N 21/17* (2006.01)

(52) U.S. Cl.
CPC ....... *G06K 9/00771* (2013.01); *G06K 9/3258* (2013.01); *H04N 7/183* (2013.01); *G01N 2021/1793* (2013.01); *G01N 2021/3513* (2013.01)

(56) References Cited

U.S. PATENT DOCUMENTS

| | | |
|---|---|---|
| 5,583,765 A * | 12/1996 | Kleehammer ......... G01G 19/03 250/338.5 |
| 5,726,450 A | 3/1998 | Peterson et al. |
| 5,831,267 A | 11/1998 | Jack et al. |
| 7,071,002 B1 | 7/2006 | Tefft et al. |
| 7,073,320 B2 | 7/2006 | Moritsugu et al. |
| 7,350,512 B1 | 4/2008 | Meacham et al. |
| 7,729,880 B1 * | 6/2010 | Mashburn ............... H04L 67/12 702/151 |
| 8,428,814 B2 | 4/2013 | Tripathi et al. |
| 9,618,381 B1 | 4/2017 | Dudar |
| 2002/0092988 A1 | 7/2002 | Didomenico et al. |
| 2004/0104345 A1* | 6/2004 | Kansakoski ....... G01N 21/3504 250/338.5 |
| 2006/0157001 A1 | 7/2006 | Rahman et al. |
| 2007/0164220 A1* | 7/2007 | Luk ........................ G01N 21/33 250/338.5 |
| 2008/0059019 A1 | 3/2008 | Delia et al. |
| 2011/0137711 A1 | 6/2011 | Singh et al. |
| 2012/0152210 A1 | 6/2012 | Reddy et al. |
| 2014/0069394 A1 | 3/2014 | Jentz et al. |
| 2014/0074385 A1 | 3/2014 | Dudar et al. |
| 2015/0114089 A1 | 4/2015 | Dudar et al. |
| 2016/0280160 A1* | 9/2016 | MacNeille ............ G05B 15/02 |

* cited by examiner

SYSTEM AND METHOD TO DETECT VEHICLE EMISSIONS NONCOMPLIANCE

CROSS REFERENCE TO RELATED APPLICATION

The present application claims priority of U.S. provisional application Ser. No. 62/251,906 filed Nov. 6, 2015, by Opus Inspection, Inc. for SYSTEM AND METHOD TO DETECT VEHICLE EMISSIONS NONCOMPLIANCE, which is hereby incorporated herein by reference in its entirety.

BACKGROUND OF THE INVENTION

The present invention is directed to a system and method for determining without recruiting vehicles, or physically or electronically connecting to vehicle systems, whether the emission systems of in-use vehicles perform according to the regulatory standards by which they were initially certified, and in particular whether particular models of vehicles are performing to their regulatory standard.

In-use vehicle emissions testing typically involves recruiting such in-use vehicles from active service and testing them on driving simulators at set conditions, such as with respect to engine load and RPMs, and/or performed when vehicle exhaust systems or computers are connected with portable emissions measurement testing equipment while the vehicle is driven on the road. These testing techniques include connections to the vehicle that are potentially detectable by the vehicle. In certain instances, vehicle manufacturers have manipulated vehicle emissions control systems, such as software controls, to circumvent the emissions controls when the vehicle on board computer system detects the vehicle is in normal on-road use, as compared to performing a regulatory compliance test drive. For example, vehicle software has been improperly configured to deactivate particular emissions equipment or functions during regular driving conditions. Such circumventions, which are generally referred to as defeat devices, violate emissions regulations and are employed to improperly obtain performance gains.

SUMMARY OF THE INVENTION

The present invention provides a system and method for determining whether in-use vehicles are performing in accordance to the regulatory standards by which they are initially certified without being recruited and without the need for physical, mechanical or electronic connection of test equipment to the vehicle. In-use vehicle emissions are measured and the vehicles are identified during normal in-use driving without mechanical or electrical connection thereto. The resulting measurements are then analyzed for compliance with regulatory emissions standards.

According to an aspect of the present invention, a method of determining and evaluating vehicle emissions performance of in-use vehicles for compliance with emissions requirements comprises measuring the emissions of a plurality of vehicles using a vehicle emission remote sensing device during in-use operation of the vehicles, identifying the vehicles by, for example, manufacturer, make, model, engine and model year, and/or family of models with a common engine system, and analyzing the measured emissions values based on identified vehicles to evaluate compliance with regulatory emissions standards. Emission measurement results may be recorded in a database for analyzing performance relative to regulatory standards.

In particular embodiments, the remote sensing device comprises a light source for projecting a beam and a detector that receives the beam, with the beam projected across and/or onto a roadway and configured to pass through emissions of the vehicles. The remote sensing device may thereby rapidly measure one or more pollutants without being mechanically or electrically connected to the vehicles.

A camera may be employed to identify the vehicles by make and model, where the camera may be used to capture images of license plates for interfacing with a database of vehicle records. Additional identifiers may be determined, including the engine type, as well as engine combustion management technology and pollution control technology associated with the vehicle. Alternatively, the camera may be utilized with a vehicle recognition program to identify the make and model of the vehicle. Still further, the vehicle speed, acceleration, thermal warm-up status, and/or other operational parameters may be determined and used in the emissions measurement and analysis.

According to another aspect of the present invention, a system for determining and evaluating vehicle emissions performance of in-use vehicles comprises a vehicle emission remote sensing device, a computer control operably integrated with the remote sensing device, a camera for capturing images of the vehicles to identify the make and model of the vehicles, and a sensor for detecting operational parameters of the vehicles, such as the speed, acceleration, or thermal warm-up status of the vehicle. The computer control may be operably connected with one or more databases, such as for obtaining identifying information of the vehicles or obtaining information regarding the regulatory emissions standards for the vehicles.

The present invention provides a system and method to rapidly perform emissions measurements of in-use vehicles being driven by the general public under normal driving use without recruitment and without any detectable connection to the vehicle, with the data being analyzed to determine whether they are performing in accordance to the regulatory standards by which they are initially certified. The in-use emissions measurements prevent any defeat devices of the vehicle from being activated, thus allowing actual emissions results to be detected. The resulting data is collected based on, for example, vehicle make and model, with the system having additionally identified the vehicle make and model from which emissions measurements are made. The system and method additionally operates to perform data analysis on the collected data to identify abnormal emissions-related conditions of a particular make and model for the purpose of in-use surveillance, thus allowing actual emissions results to be detected, determined and compared for compliance with regulatory standards.

These and other objects, advantages, purposes and features of this invention will become apparent upon review of the following specification in conjunction with the drawings.

DESCRIPTION OF THE PREFERRED EMBODIMENTS

Figure 1:
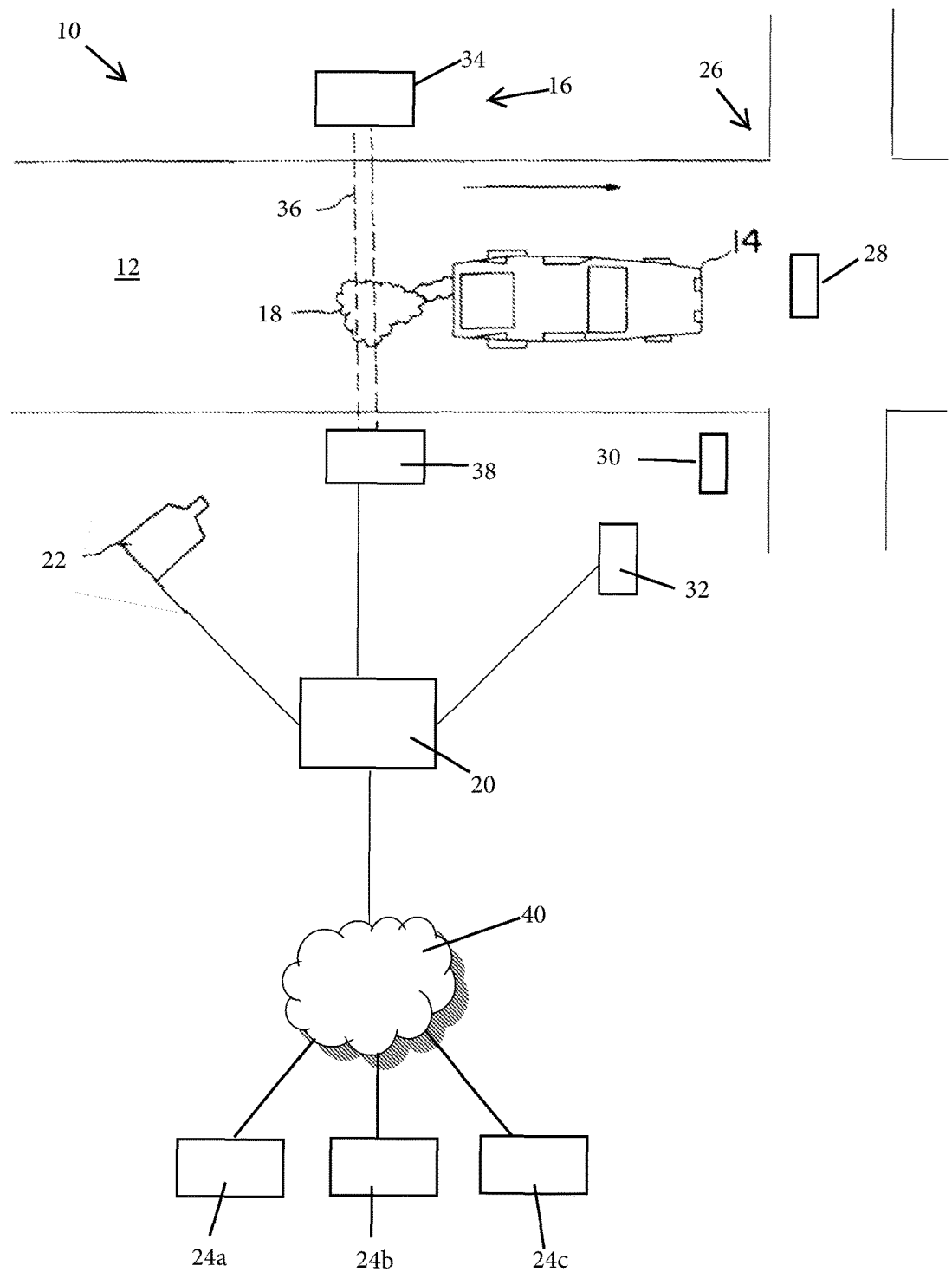
FIG. 1 is a schematic illustration of a system for detecting vehicle emissions noncompliance in accordance with an aspect of the present invention.

The present invention will now be described with reference to the accompanying figures, wherein the numbered elements in the following written description correspond to like-numbered elements in the figures. As understood from FIG. 1, a system 10 for detecting vehicle emissions non-compliance is illustrated, with system 10 operating to measure vehicle emissions of in-use vehicles during normal operation and analyze the results to determine whether particular vehicles are performing in accordance with their initial regulatory standard certifications. System 10 thus incorporates components disposed adjacent roadway 12 over which vehicles travel, such as a vehicle emission remote sensing device (or "RSD") 16 that is operable to analyze and evaluate characteristics, constituencies or compositions of the exhaust plume or emissions 18 discharged by vehicles, such as vehicle 14. System 10 further includes a computing device or computer 20 integrated with RSD 16 for analyzing emissions 18, and a camera 22 that is operatively connected with computer 20 for capturing images of vehicle 14, with computer 20 being networked with various databases 24a, 24b, 24c that may include, for example, information on vehicle regulatory standards, vehicle fuel economy ratings, and/or be used in the identification of vehicles. The in-use emissions measured and analyzed by system 10 are thus the real world emissions or real driving emissions of vehicle 14 when it is being normally operated.

In operation, system 10 determines operating parameters of the vehicle, such as its speed and acceleration, and analyzes emissions 18 via RSD 16 based on the operating parameters, as well as identifies the make and model of vehicle 14 via camera 22. This data is collected over time for numerous makes and models of vehicles during normal driving conditions, including for numerous samples of the same make and model, and including the same or equivalent vehicle years. The data is then compared to regulatory standards by which such vehicles were initially certified to thereby evaluate whether the particular models of vehicles are performing to the regulatory standard. Accordingly, emissions results and analysis can be performed without connecting vehicles to an emissions test device, and with actual driving conditions being analyzed to determine whether the vehicles are in compliance with their appropriate regulatory standard, such as the initial vehicle type emissions requirements.

In operation, the detection components of system 10 may be positioned at locations in which vehicles to be evaluated are accelerating to thereby obtain measurements that may be more reflective of actual pollution. In one embodiment, for example, the detection components of system 10 are positioned proximate a freeway entry ramp to detect emissions during acceleration of vehicles on to the freeway. Alternatively, in the embodiment of FIG. 1, system 10 is shown as being positioned proximate an intersection 26, where intersection 26 may include a traffic signal, such as a traffic light 28, a stop sign 30, or the like. Accordingly, RSD 16 is thus operable to evaluate emissions 18 during periods in which vehicle 14 undergoes non-steady state operation, such as when vehicle 14 is accelerating after having stopped or accelerating to enter a freeway. System 10 is therefore shown in the illustrated embodiment to include a sensor 32, where sensor may comprise a vehicle speed sensor, such as a radar and/or laser type sensor. Sensor 32 is shown as being operatively connected with computer 20, where sensor 32 may additionally provide time data for determination of acceleration or provide acceleration data directly, or computer 20 may itself make acceleration determinations based simply on received velocity data. The driving mode of vehicle 14 may thus be determined, where the driving mode impacts vehicle emissions and can be taken into consideration during data analysis of the emissions testing results.

As noted, RSD 16 is constructed to be an apparatus for remote analysis or measurement of vehicle emissions or exhaust gas, and may be constructed as a conventional vehicle emission remote sensing device. In the illustrated embodiment, RSD 16 includes a light source 34 that projects a beam 36, with beam 36 aligned to pass through exhaust emissions plume 18. Although beam 36 is illustrated as extending across roadway 12, it should be appreciated that alternative configurations may be employed, including where a beam is projected onto the roadway rather than across the roadway. Light source 34 may supply infrared ("IR") radiation, with source 34 comprising a broad band IR source, and/or may comprise a narrow-band light source, such as to supply a narrow-band light or ultraviolet ("UV") radiation. The passage of the beam 36 through the exhaust gas plume 18 results in the selective partial absorption of various wavelengths within the broad band beam, the selective absorption occurring because of the presence of $NO_x$, water vapor, $CO_2$, CO, HC (hydrocarbons), and other species within the exhaust gas. As is known by those of skill in the art, each of the aforementioned species absorbs infrared radiation at or near a known wavelength or wavelengths. RSD 16 thus comprises a fast emissions analyzer that is neither mechanically nor electrically connected to the vehicle 14 undergoing emissions measurement and analysis.

After passing through the plume 18, the beam 36 passes into a receiver or detector 38, where the detector 38 may include a beam integrator or diffuser. The diffused beam is subsequently applied to a plurality of narrow band filters, each of the filters corresponding to a measurement channel. Each filter is selected so as to pass a predetermined narrow band of wavelengths to a focal plane having a plurality of photodetectors individually tuned for a specific pollutant. Each photodetector outputs an electrical signal to an input of a corresponding measurement channel, and may include suitable analog electronics and an analog-to-digital convertor.

There can be, for example, numerous spectral measurement channels, depending upon the number of pollutants and reference channels that are desired to be monitored. For example, there can be an NO spectral channel (having a filter with a pass band centered on about 5.26 micrometers), an $H_2O$ spectral channel (having a filter with a pass band centered on about 5.02 micrometers), a first reference, or $CO_2$, spectral channel (having a filter with a pass band centered on about 4.2 micrometers), a CO spectral channel (having a filter with a pass band centered on about 4.6 micrometers), an HC spectral channel (having a filter with a pass band centered on about 3.3 micrometers), and a second reference spectral channel having a filter with a pass band centered on about 3.8 micrometers. Additional channels to measure other pollutants can also be added if desired.

Computer 20 is integrated with RSD 16 and operable to provide the required signal processing of the outputs of detector 38. A vehicle emission remote sensing device employed in the present invention may thus be constructed as disclosed in either of U.S. Pat. No. 5,210,702 or 5,831,267, which are both hereby incorporated herein by reference in their entireties. It should be appreciated, however, that alternative arrangements and/or devices for measuring in-use emissions of vehicles during normal operation may be employed within the scope of the present invention, including without physical, mechanical or electrical connection to the vehicle. Accordingly, it should be appreciated that alternative vehicle emission remote sensing devices may be employed for remotely measuring in-use vehicle emissions within the scope of the present invention.

In addition to the speed/acceleration of vehicle 14, system 10 may obtain and evaluate additional information regarding operating parameters of vehicle 14. For example, computer 20 may receive information regarding the thermal warm-up status of vehicle 14, such as by way of wireless temperature or thermal sensors, such as infrared temperature sensors, or the like. Such a sensor may be separately located or incorporated into sensor 32, where sensor 32 may thus comprise various instruments for obtaining differing data. Accordingly, RSD 16 may additionally consider the thermal warm-up state of vehicle 14 during analysis of the emissions 18 of the vehicle 14. Still further, additional operational parameters may be determined and used in evaluating the vehicle emissions, including the vehicle load, and including the ambient weather conditions during evaluation.

In the illustrated embodiment, and as previously noted, computer 20 is further operatively connected with camera 22 and one or more databases, such as illustrated databases 24a, 24b and 24c, which may comprise separate computing devices or networks that are connected with computer 20 by a network or internet 40. Camera 22 is used to capture images of vehicle 14 for the purpose of identifying the vehicle 14. It should be understood that the identification of the vehicles may be based on or according to various vehicle characteristics or commonalities. This includes, for example, the manufacturer, make, model, engine and model year or family of models with a common engine system or emissions system, or any combination thereof. For example, different brands of vehicles may share the same engine and emissions components whereby the present system may be employed to compare the actual in-use emissions of vehicles sharing the same engine and emissions components to their respective regulatory standard certification. Accordingly, it should be understood that reference herein to identifying vehicles and comparison of makes and models may encompass identifying and comparison of vehicles sharing common features for emissions evaluation purposes, including without limitation engine size, engine combustion technology and emissions systems.

Camera 22 may be used, for example, to capture an image of the license plate of vehicle 14 with computer 20 configured to access and retrieve or receive information based thereon from database 24a, where database 24a may comprise a vehicle database of vehicle registration data from secretary of state records, records of a state department of motor vehicles, or other such data from a governmental or regulatory body or the like. System 10 may additionally include or incorporate a governmental or other database containing vehicle fuel economy data and standards. Alternatively or additionally, camera 22 and/or computer 20 may incorporate a vehicle or object recognition program or software for determining a vehicle make and model without the need to access governmental records, where such a program is operable to directly or indirectly, such as via a database lookup, determine the vehicle make and model. The obtained data or ascertained information may further include vehicle engine size information, combustion management technology of the vehicle, and/or pollution control information of the vehicle. Still further, accessed data, such as from a governmental body, may further include information regarding the emissions inspection history of the particular vehicle. The vehicle inspection history information may be used, for example, to confirm that the particular vehicle under evaluation is considered to be a normally operating and configured representative example of the particular make and model.

In the illustrated embodiment, system 10 is additionally configured to record results of vehicle emissions analysis performed by RSD 16 for each vehicle so evaluated, with the data recorded in database 24b. The data may be recorded, for example, based on vehicle make and model. Accordingly, system 10 is able to analyze emissions 18 from vehicles 14 that pass by on road 12. It should thus be appreciated that system 10 is operable to obtain significant data collection on particular makes and models as the vehicles pass by system 10 during normal operating conditions. The acquired data may then be analyzed to obtain emissions information directed to a particular make and model of vehicle based on the population of such vehicles for which RSD 16 has analyzed emissions. In operation, system 10 may be located at a particular freeway entry ramp or intersection 26 through which the same vehicle may travel multiple times. Accordingly, system 10 may account for this by limiting the subsequent data analysis to the emissions analysis results of unique vehicles.

Figure 2:
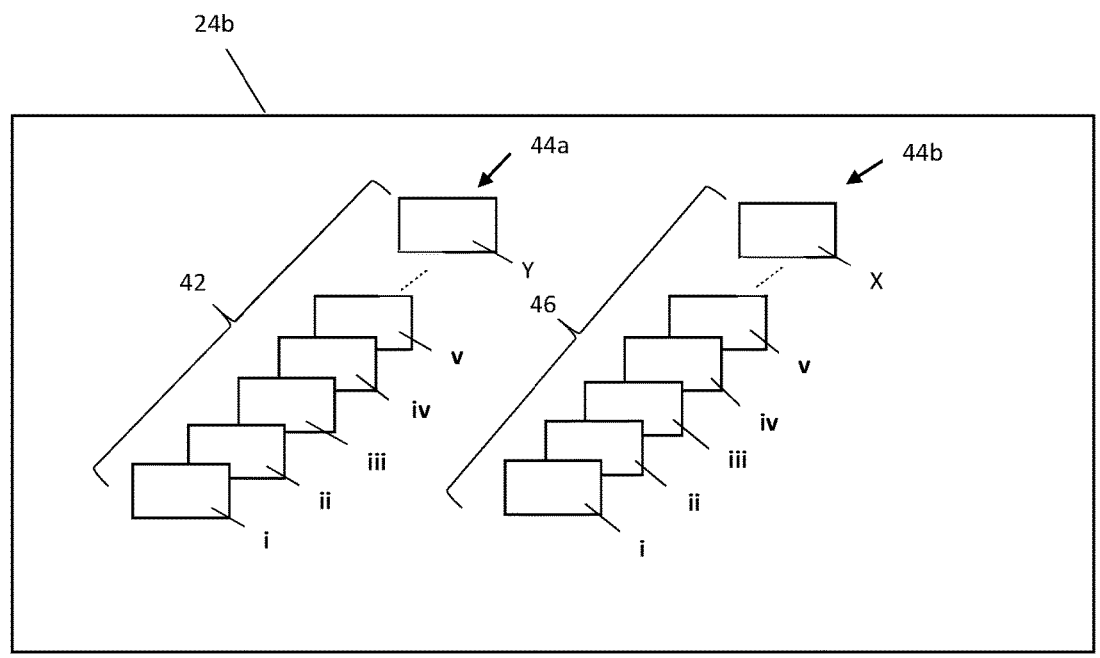
FIG. 2 is a schematic illustration of vehicle emissions analysis results for different versions of particular makes and models of vehicles that are determined and recorded by the system of FIG. 1 for performing data analysis.

As understood from FIG. 2, various emissions analysis results 42 for a particular vehicle make and model 44a are recorded in database 24b, where results 42 are obtained for y different examples of the particular make and model 44a. Similarly, results 46 corresponding to a different vehicle make and model 44b are recorded in database 24b, where results 46 are obtained for x different examples of the particular make and model 44b. It should be readily appreciated that emissions data for numerous different types of makes and models of vehicles can be readily obtained by locating system 10 at road 12. Moreover, results may be recorded for different driving modes and/or parameters. For example, results may be obtained, determined, and recorded during vehicle acceleration, at a constant velocity of the vehicle, during vehicle warm-up state, or the like.

Still further, system 10 may access or receive data regarding the regulatory standards under which an identified vehicle 14 was certified for its emissions output based on the particular identified make and model of the vehicle 14. For example, computer 20 may access database 24c, with database 24c comprising a standards database containing data information and records regarding the emissions testing results pursuant to regulatory standards testing and/or regulatory standards requirements, such as the vehicle type approval or vehicle certification.

System 10 is then additionally employed to perform data analysis on the collected data for particular vehicles, such as particular makes and models, relative to their regulatory standard. Such data analysis may include determining the various mean, mode and median, and various standard deviations, of particular pollutants that have been measured for a given population of analyzed vehicles by make and model. As noted, the analysis may additionally compare and/or take into consideration different engine sizes, engine combustion management technologies, and pollution control technologies, as well as manufacturer or government agency measured fuel economy over specified driving cycles. Still further, the data analysis may also include or comprise comparisons of particular makes and models of vehicles to other similar classes or platforms of vehicles produced by the same or other manufacturers. This may include, for example, comparisons of mid-sized passenger sedans, economy cars, sport utility vehicles, trucks, and the like. This data analysis may be used to identify abnormal emissions-related conditions of a particular make and model relative to their regulatory standards for the purpose of in-use surveillance. Upon detection of emissions levels of a particular make and model substantively deviating from the regulatory standards, an appropriate regulatory body may be informed, such as for the performance of confirmatory testing and/or enforcement actions. System 10 thus enables rapid emissions measurement of in-use vehicles being driven by the general public during normal use and without any detectable connection to the vehicle such that any defeat devices of the vehicle would not be activated, and thus allowing actual emissions results to be detected, determined and compared for compliance with regulatory standards.

Statistical analysis may also be performed on emissions analysis by RSD 16 in view of the recorded data to enable determination as to whether a particular result is errant due, for example, to a damaged emissions system of the vehicle 14 as opposed to operating in the manner as constructed by the vehicle manufacturer. Still further, statistical analysis may enable determination that a result is errant due to testing influences, such as beam 36 passing through an inadequate plume 18.

It should be appreciated that numerous alternatives to system 10 may be employed within the scope of the present invention. For example, although system 10 is disclosed in connection with a computer 20 that is generally local to road 12, an alternative computer may be employed in which information is transmitted over a network, such as network 40, for remote data processing. Moreover, more than one computer may be employed in system 10. Still further, alternative databases and/or numbers of databases may be used for storing and/or retrieving information, including utilizing data information locally stored on a computer rather than employing remote databases.

Moreover, other changes and modifications in the specifically described embodiments can be carried out without departing from the principles of the present invention which is intended to be limited only by the scope of the appended claims, as interpreted according to the principles of patent law including the doctrine of equivalents.

The embodiments of the invention in which an exclusive property or privilege is claimed are defined as follows:

1. A method of determining and evaluating vehicle emissions performance of in-use vehicles for compliance with emissions requirements, the method comprising:
   measuring the emissions of a plurality of vehicles using a vehicle emission remote sensing device during in-use operation of the plurality of vehicles to obtain a plurality of emission analysis results;
   identifying the plurality of vehicles associated with the plurality of emission analysis results by vehicle make and model;
   recording the plurality of emission analysis results based on vehicle make and model in a database to obtain a plurality of emission analysis results recorded based on vehicle make and model for at least one particular make and model; and
   analyzing the plurality of emission analysis results by population for a particular make and model to evaluate the vehicle emission performance for the particular make and model by population.

2. The method of claim 1, wherein the remote sensing device comprises a light source for projecting a beam and a detector that receives the beam, and wherein the remote sensing device is disposed adjacent a roadway with the beam being projected across and/or onto the roadway and configured to pass through emissions of the vehicles.

3. The method of claim 1, wherein said measuring the emissions of a plurality of vehicles comprises measuring selected pollutants of the emissions.

4. The method of claim 1, wherein said identifying the vehicles comprises using a camera to identify the vehicle.

5. The method of claim 4, wherein said camera captures images of vehicle license plates and said method further comprises accessing a vehicle database to identify the vehicle by its license plate.

6. The method of claim 4, wherein said camera captures images of the vehicles and the vehicles are identified via an object recognition program.

7. The method of claim 1, further including sensing an operational parameter of the vehicles during in-use operation of the vehicles.

8. The method of claim 7, wherein said sensing an operational parameter of the vehicles includes sensing the speed, acceleration, and/or thermal-warm up state of the vehicles.

9. The method of claim 1, wherein said analyzing the measured emissions values comprises analyzing a database of measured emissions values.

10. The method of claim 9, wherein the database of measured emissions values includes data based on vehicle make and model, vehicle operational parameters and/or vehicle engine size.

11. The method of claim 1, wherein said analyzing the measured emissions values further comprises comparing measured emissions values by population for a particular make and model to initial vehicle type emissions requirements based on the vehicle make and model for compliance with regulatory emissions standards.

12. The method of claim 1, wherein said identifying the vehicles comprises identifying at least one of the manufacturer, make, model, model year, engine or emissions system of the vehicles.

13. A system for determining and evaluating vehicle emissions performance of in-use vehicles for compliance with emissions requirements, the system comprising:
   a vehicle emission remote sensing device, said remote sensing device operable to measure vehicle emissions of a plurality of vehicles with the remote sensing device configured to be positioned adjacent a roadway for measuring the emissions of a plurality of vehicles passing thereby;
   a computer control, said computer control operably integrated with said remote sensing device;
   a camera, said camera being operable to capture images of vehicles for which emissions are measured by said remote sensing device to identify the vehicles with said camera being operably connected with said computer control to identify the vehicles by make and model, with the camera configured to being positioned adjacent the roadway with said remote sensing device;
   a sensor, said sensor being operable to detect operational parameters of vehicles for which emissions are measured by said remote sensing device with said sensor being operably connected with said computer control and configured to being positioned adjacent the roadway with said remote sensing device, wherein the operational parameters include the speed and/or acceleration of the vehicles;
   said computer control being operable to access a database of vehicle emission results determined by said remote sensing device with the vehicle emission results recorded by make and model of vehicle and to analyze a population of vehicle emissions measurement data for a particular make and model of vehicle to evaluate the vehicle emission performance for the particular make and model by population.

14. The system of claim 13, wherein said remote sensing device comprises a light source for projecting a beam and a detector that receives the beam, and wherein said remote sensing device is configured to be disposed adjacent the roadway with the beam being projected across and/or onto the roadway and configured to pass through emissions of the vehicles.

15. The system of claim 13, wherein said camera is operable to capture images of the license plates of the vehicles, and wherein said computer control is operably connected with a vehicle database for identifying the vehicle make and model by its license plate.

16. The system of claim 13, further including a vehicle recognition program, and wherein said camera is operable to capture images of the vehicle with said vehicle recognition program being operable to identify the vehicle make and model.

17. The system of claim 13, wherein said computer control is operably connected with a standards database, and wherein said standards database comprises data regarding vehicle emissions requirement standards based on vehicle configurations.

18. The system of claim 13, wherein said sensor is further operable to detect the thermal warm-up status of the vehicles.

19. The system of claim 13, wherein said computer control comprises a plurality of computer devices.

20. The system of claim 13, wherein said sensor includes a radar and/or a laser for determining vehicle speed and/or acceleration.

* * * * *